US011253826B2

(12) United States Patent
Jenzsch et al.

(10) Patent No.: US 11,253,826 B2
(45) Date of Patent: Feb. 22, 2022

(54) COMBINATION STIRRER

(71) Applicant: HOFFMANN-LA ROCHE INC., Little Falls, NJ (US)

(72) Inventors: Marco Jenzsch, Penzberg (DE); Max Lechner, Penzberg (DE); Michael Pohlscheidt, Carlsbad, CA (US); Christoph Reese, Munich (DE); Alexander Scholz, Karlsruhe (DE); Hermann Tebbe, Schlehdorf (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 10 days.

(21) Appl. No.: 16/103,341

(22) Filed: Aug. 14, 2018

(65) Prior Publication Data
US 2019/0168177 A1  Jun. 6, 2019

Related U.S. Application Data

(62) Division of application No. 13/375,153, filed as application No. PCT/EP2010/003356 on Jun. 2, 2010, now Pat. No. 10,076,731.

(30) Foreign Application Priority Data
Jun. 5, 2009  (EP) .................................... 09007457

(51) Int. Cl.
B01F 7/00 (2006.01)
C12M 1/06 (2006.01)

(52) U.S. Cl.
CPC ........ B01F 7/00641 (2013.01); B01F 7/0025 (2013.01); B01F 7/00266 (2013.01); B01F 7/00341 (2013.01); C12M 27/02 (2013.01)

(58) Field of Classification Search
CPC .. B01J 19/18; B01J 2219/185; B01J 19/0066; B01J 2219/00768; B01J 2219/00189;
(Continued)

(56) References Cited

U.S. PATENT DOCUMENTS 3,445,342 A  5/1969  Freedman
4,395,133 A  7/1983  Clevenholm et al.
(Continued)

FOREIGN PATENT DOCUMENTS

EP  0 049 229 B1  4/1982
EP  0 200 886 A1  11/1986
(Continued)

OTHER PUBLICATIONS

Mirro et al. "Which Impeller Is Right for Your Cell Line?" *BioProcess Inti.* 7(1): (Jan. 2009).
(Continued)

Primary Examiner — Sally A Merkling
(74) Attorney, Agent, or Firm — Morrison & Foerster LLP

(57) ABSTRACT

The present patent application describes a stirrer comprising a combination of at least one axially-conveying element and at least one radially-conveying element relative to the rotary shaft of the stirrer wherein the largest diameter of the at least one axially-conveying element is equal to or less than the inner diameter $d_i$ of the radially-conveying element. In one embodiment the stirrer according to the invention is a combination of one anchor stirrer with at least one inclined-blade stirrer. Furthermore the use of the stirrer according to the invention for the culture of cells in a dialysis method is described.

8 Claims, 7 Drawing Sheets

(58) Field of Classification Search
CPC ........... B01J 2219/00779; C12M 27/02; B01F 3/04531; B01F 7/0025; B01F 7/00383; B01F 7/00641; B01F 7/00341; B01F 7/00266
USPC ................................................. 422/135, 225
See application file for complete search history.

(56) References Cited

U.S. PATENT DOCUMENTS

| | | | |
|---|---|---|---|
| 4,438,074 A * | 3/1984 | Wilt | B01J 19/18 366/171.1 |
| 4,552,461 A | 11/1985 | Ott et al. | |
| 4,699,740 A | 10/1987 | Bollenrath | |
| 5,286,646 A | 2/1994 | Kearns et al. | |
| 5,342,763 A | 8/1994 | Swartz | |
| 5,633,165 A | 5/1997 | Swartz | |
| 7,374,333 B2 | 5/2008 | Eisenkraetzer et al. | |
| 7,384,783 B2 | 6/2008 | Kunas et al. | |
| 7,682,067 B2 | 3/2010 | West et al. | |
| 7,879,599 B2 | 2/2011 | Goodwin et al. | |
| 7,887,765 B2 * | 2/2011 | Varela-Fuentes | B01J 4/001 261/83 |
| 7,901,934 B2 | 3/2011 | Kunas et al. | |
| 8,124,403 B2 | 2/2012 | Goodwin et al. | |
| 8,187,867 B2 | 5/2012 | Kunas et al. | |
| 8,603,805 B2 | 12/2013 | Goodwin et al. | |
| 8,623,640 B2 | 1/2014 | Kunas et al. | |
| 10,076,731 B2 | 9/2018 | Jenzsch et al. | |
| 2001/0055237 A1 | 12/2001 | Kubera et al. | |
| 2004/0234435 A1 | 11/2004 | Bickham et al. | |
| 2009/0081723 A1 | 3/2009 | Amano et al. | |
| 2012/0070860 A1 | 3/2012 | Jenzsch et al. | |
| 2012/0135464 A1 | 5/2012 | Alisch et al. | |

FOREIGN PATENT DOCUMENTS

| | | |
|---|---|---|
| EP | 0 200 886 B1 | 11/1986 |
| EP | 0 224 800 A2 | 6/1987 |
| EP | 0 224 800 A3 | 6/1987 |
| EP | 0 224 800 B1 | 6/1987 |
| EP | 0 873 781 A1 | 10/1998 |
| EP | 1 588 758 A1 | 1/2005 |
| EP | 2 039 754 A1 | 3/2009 |
| EP | 2 143 801 A1 | 1/2010 |
| JP | 61-200842 A2 | 9/1986 |
| JP | 3-48904 A | 3/1991 |
| JP | 8-252445 A | 10/1996 |
| JP | H-10-511306 A | 11/1998 |
| JP | 2004-121256 A | 4/2004 |
| JP | 2005-305431 A | 11/2005 |
| JP | 2008-536686 A | 9/2008 |
| JP | 2009-72133 A | 4/2009 |
| JP | 2012-533419 A | 12/2012 |
| WO | WO-1994/012630 A2 | 6/1994 |
| WO | WO-1994/012630 A3 | 6/1994 |
| WO | WO-2001/41919 A1 | 6/2001 |
| WO | WO-2005/104706 A2 | 11/2005 |
| WO | WO-2008/120643 A1 | 9/2008 |
| WO | WO-2010/139470 A1 | 12/2010 |

OTHER PUBLICATIONS

Nienow, A.W. "Agitators for Mycelial Fermentations," *Trends in Biotechnology* Elsevier Publications, Cambridge, 8(8):224-233, (1990).
Nomura et al. "Development and Mixing Characteristics of Folding Anchor Impeller for Round Bottomed Flask," *J. Chem. Eng.* 29(1):134-138, (1996).
International Preliminary Report on Patentability dated Dec. 6, 2011 for related PCT Patent Application No. PCT/EP2010/003356. 9 pages.
International Search Report dated Sep. 9, 2010 for related PCT Patent Application No. PCT/EP2010/003356, 4 pages.
Written Opinion of the International Searching Authority dated Sep. 9, 2010 for related PCT Patent Application No. PCT/EP2010/003356, 8 pages.

* cited by examiner g)

h)

i)

j)

COMBINATION STIRRER

CROSS-REFERENCE TO RELATED APPLICATIONS

This application is a Divisional of U.S. patent application Ser. No. 13/375,153, internationally filed Jun. 2, 2010, issued as U.S. Pat. No. 10,076,731 on Sep. 18, 2018, which is a National Stage Application under 35 U.S.C. § 371 of International Application No. PCT/EP2010/003356, filed Jun. 2, 2010, which claims priority to and the benefit of European Patent Application No. 09007457.6, filed Jun. 5, 2009, the entire disclosures of each of which are incorporated herein by reference in their entirety.

Herein is reported an agitator, a device comprising the agitator and the use of the agitator for the cultivation of cells. The agitator comprises at least one axially-conveying element and at least one radially-conveying element, such as the combination of an anchor impeller as a radially-conveying element and one or more inclined-blade impeller(s) as an axially-conveying element. The use of the agitator results in an improved mixing and in particular a lower biofouling in dialysis processes as well as a higher mass transfer rate.

TECHNOLOGICAL BACKGROUND

The production of recombinant proteins, vaccines and antibodies with the aid of prokaryotic and eukaryotic cells plays an essential role in modern pharmaceutical production. To produce complex post-translationally modified proteins and antibodies animal derived cells are primarily used. However, the use of animal derived cells sets high demands for the fermentation process due to the specific characteristics of these cells such as e.g. the culture medium, the sensitivity towards limitation and inhibitions (for example by lactate, $CO_2$, ammonium etc.), the sensitive outer membrane (shear stress), the low specific rates and the sensitivity towards variations in the culture conditions (e.g. due to local inhomogeneities, pH variations, $pO_2$ variations etc.). These properties have to be taken into consideration when designing bioreactors and for process control.

In recent years various types of reactors for culturing cells have been developed. Irrespective of the type, the reactor must be able to fulfill the following basic technical functions: adequate suspension as well as homogenization, adequate material and heat transport as well as a minimal shear stress on the cells. The stirred-tank reactor is especially suitable for industrial use. In this reactor the necessary energy for fulfilling the basic functions is introduced by mechanical stirring.

In order to achieve high product titer and specification compliant product quality, the operating mode of the reactor in particular plays an important role in addition to cell line development, media composition and design of the reactor. Generally the following operating modes are employed: batch processes, fed batch processes, continuous processes with or without cell retention (for example perfusion or chemostat) as well as semi-continuous processes such as e.g. internal or external dialysis.

To prevent nutrient limitations feed solutions are added to a reactor in the form of concentrated solutions (so-called fed batch processes). To avoid inhibition by end products of the cell's metabolism the products of the cell's metabolism have to be removed from the reactor or from the culture medium in the reactor. This can be carried out for example by perfusion or dialysis. In the case of dialysis one differentiates between external or internal dialysis.

EP 1 474 223 reports a dynamic mixer. An animal cell culturing device comprising a container for the uptake of a cell suspension, a device for feeding- and discharge of gas into the cell suspension, and a device for production of a current in the cell suspension is reported in DE 10 2005 053 333. Method and apparatus for cell culture is reported in EP 0 224 800. Nomura, T., et al., J. Chem. Eng. Jap. 29 (1996) 134-138 report development and mixing characteristics of folding anchor impeller for round bottom flask. An impeller draft tube agitation system for gas-liquid mixing in a stirred tank reactor is reported in WO 01/41919. In U.S. Pat. No. 4,438,074 a continuous polymerization reactor is reported. An agitation system and method for gas transfer into liquids is reported in EP-A 0 200 886. In EP-B 0 049 229 a cooking apparatus having a stirring device is reported.

SUMMARY OF THE INVENTION

The agitator as reported herein at least i) allows for rapid mixing of culture media compared to other stirrers e.g. for introducing correction agents such as acids or bases via the liquid or cultivation medium surface, ii) reduces foam formation, iii) reduces biofouling in dialysis processes, and iv) increase mass transfer in dialysis processes due to the direct orthogonal flow against the dialysis module as a result of the combination of differently conveying elements.

Herein is reported an agitator (combination stirrer) comprising at least one axially-conveying element and at least one radially-conveying element relative to the shaft of the agitator wherein the largest diameter of the at least one axially-conveying element is equal to or less than the inner diameter $d_i$ of the radially-conveying element.

One aspect as reported herein is an agitator, comprising
  one radially-conveying element comprising at least two stirrer blades, and
  one or more axially-conveying elements each comprising at least two stirrer blades,
  wherein the stirrer blades of the radially-conveying element are parallel to each other and to the shaft axis of the agitator, and
  wherein the outer diameter of all axially-conveying elements is equal to or less than the inner diameter of the radially-conveying element, and
  wherein all axially-conveying elements are individually connected to the radially-conveying element, and
  wherein all axially-conveying elements are located within the radially-conveying element, and
  wherein all conveying elements have a fixed spatial orientation relative to each other and to the shaft axis of the agitator.

In one embodiment the agitator comprises 1 to 5 axially-conveying elements, or in another embodiment 1 to 3 axially-conveying elements, or in also an embodiment 1 or 2 axially-conveying elements. In one embodiment the at least one axially-conveying element is situated in the upper four fifths of the agitator determined from the head of the agitator and is at a maximum distance of $h_{4/5}$ to the head of the agitator. In also an embodiment one axially-conveying element is located at a maximum distance of 80% from the top of the blades of the radially-conveying element (i.e. at a maximum distance of 0.8 h) and/or one axially-conveying element is located at a maximum distance of 20% from the top of the blades of the radially-conveying element (i.e. at a maximum distance of 0.2 h). In a further embodiment the at least one axially-conveying element and the at least one radially-conveying element form together a single element. In another embodiment opposing stirrer blades of the radially-conveying element are linked to each other by two opposite stirrer blades of an axially-conveying element. In one embodiment the diameter of all axially-conveying elements is identical. In another embodiment the axially-conveying elements is selected independently of each other from a propeller agitator, pitched-blade agitator, or inclined-blade agitator.

If the diameter of the axially-conveying element is less than inner diameter of the radially-conveying element the spatial distance between the tip of the stirrer blade of the axially-conveying element and the inner edge of the radially-conveying element is bridged by a connector. The connector is in one embodiment selected from wire, rod, sheet plate and disc.

In a further embodiment all conveying elements, i.e. the axially-conveying as well as the radially-conveying elements, rotate with the same number of rotations per time unit around the shaft axis of the agitator when the agitator is operated in a cultivation vessel. In one embodiment the conveying elements are permanently joined together and the agitator consists of one part, i.e. both elements are driven by the same rotary shaft and have the same number of rotations per time unit around the shaft axis of the agitator.

The ratio d/D of agitator diameter (d) to cultivation vessel diameter (D) is in one embodiment of from 0.2 to 0.8, in another embodiment of from 0.3 to 0.6, and in also an embodiment of from 0.33 to 0.5. In another embodiment the ratio hid of blade height (h) to agitator diameter (d) is of from 0.5 to 5, in another embodiment of from 1 to 4, and in also an embodiment of from 1 to 3. In yet another embodiment the ratio b/d of agitator blade width (b) to agitator diameter (d) is of from 0.05 to 0.3, in another embodiment of form 0.1 to 0.25. The term "of from . . . to" denotes a range including the listed boundary values. In another embodiment the stirrer diameter (d) is selected from 500 mm, 600 mm, 700 mm, 800 mm, 1000 mm, 1200 mm, 1400 mm, 1600 mm, 1800 mm and 2000 mm. In a further embodiment the agitator blade width (b) is selected from, 42 mm, 60 mm, 89 mm, 108 mm, 133 mm.

In one embodiment the one radially-conveying element is an anchor impeller. In a further embodiment the elements connecting the individual stirrer blades of the radially-conveying element are the stirrer blades of the axially-conveying element (connecting stirrer blades). In an embodiment the connecting stirrer blades act of from 20% to 100% as an axially-conveying element, in another embodiment of from 50% to 100% as an axially-conveying element, and in also an embodiment of approximately 100% as an axially-conveying element. The term "approximately" denotes that the given value is the center point of a range spanning plus/minus 10% around the value. If this value is a percentage value then "approximately" denotes also means plus/minus 10%, but the value 100% cannot be exceeded.

In a further embodiment the axially-conveying element is an inclined-blade stirrer. In another embodiment the radially-conveying element is an anchor impeller and the axially-conveying element is an inclined-blade stirrer where the inclined-blade stirrer is designed to act as a connecting element of blades of the anchor impeller. In another embodiment all opposing blades of the radially-conveying element are connected to each other via blades of an axially-conveying element. In one embodiment the agitators consists of a combination of one or two axially-conveying elements and one radially-conveying element relative to the shaft axis of the agitator. In another embodiment the radially-conveying element is an anchor impeller and the axially-conveying elements are two inclined-blade stirrers wherein blades of the inclined-blade stirrers are designed to act as connecting elements of opposing anchor impeller blades.

The ratio $h_{SB}/b$ of the height of the axially-conveying element and the width of the blades of the radially-conveying element is of from 0.5 to 4, in another embodiment of from 0.8 to 3, and also in an embodiment of from 1 to 2. In another embodiment the pitch of the stirrer blades of the inclined-blade stirrer is of from 10° to 80°, in a further embodiment of from 24° to 60°, and in also an embodiment of from 40° to 50° relative to the shaft axis of the agitator.

In one embodiment the radially-conveying element has of from 1 to 8 stirrer blades, in another embodiment of from 1 to 4 stirrer blades, and also in an embodiment 4 stirrer blades. The axially-conveying element has in one embodiment of from 1 to 10 stirrer blades, in another embodiment of from 2 to 6 stirrer blades, and also in an embodiment 4 stirrer blades. In another embodiment the radially-conveying and axially-conveying elements have the same number of stirrer blades.

In one embodiment the locking device on the shaft of the agitator is in the lower third seen from the head of the stirrer and has a ratio $h_u/h_m$ of the height of the reduction part ($h_u$) and the height of the tightening lid ($h_m$) of from 0.05 to 1, in another embodiment of from 0.2 to 0.8, and in also an embodiment of from 0.3 to 0.5.

In one embodiment the agitator has a height of at least 200 mm, in another embodiment of from 200 mm to 5000 mm. In another embodiment the height of the agitator is the height h of the blades of the radially-conveying element.

Herein is further reported as an aspect a device comprising the agitator as reported herein and a cultivation vessel. In one embodiment the agitator and the cultivation vessel form a functional unit, i.e. the agitator is within the cultivation vessel and can rotate within the cultivation vessel without any spatial limitation. In one embodiment the device further comprises a dialysis module. In one embodiment the cultivation vessel is a stirred tank reactor. In a further embodiment the cultivation vessel is an aerated or submerse gassed stirred tank reactor. In one embodiment the cultivation vessel comprises of from 2 to 4 baffles. In another embodiment the baffles are spaced equidistally around the circumference of the inside surface of the cultivation vessel.

The ratio d/D of agitator diameter (d) to cultivation vessel diameter (D) is in one embodiment of from 0.2 to 0.8, in another embodiment of from 0.3 to 0.6, and in also an embodiment of from 0.33 to 0.5. In another embodiment the ratio H/D of filling height of the reaction vessel (H) to cultivation vessel diameter (D) is of from 1.0 to 2.5, in a further embodiment of from 1.1 to 2.0, and also in an embodiment of from 1.4 to 1.8. In one embodiment the cultivation vessel has a working volume of from 5 l to 25,000 l.

Herein is also reported as an aspect the use of the agitator or the device as reported herein. In one embodiment the use is for the cultivation of cells for the production of a polypeptide, i.e. for the cultivating of cells expressing a polypeptide encoded by a heterologous nucleic acid. In one embodiment the cultivating is a dialysis. In a further embodiment the cultivating is carried out in a submersed gassed stirred tank reactor. In another embodiment the cell is a eukaryotic cell. In also an embodiment the cell is a mammalian cell. In yet a further embodiment the cell is selected from a CHO cell, a BHK cell, an NSO cell, a COS cell, a PER.C6 cell, a Sp2/0 cell, and a HEK 293 cell. In one embodiment the polypeptide is an antibody. In a further embodiment the antibody is an antibody against CD20, CD22, HLA-DR, CD33, CD52, EGFR, G250, GD3, HER2, PSMA, CD56, VEGF, VEGF2, CEA, Lewis Y antigen, the IL-6 receptor or the IGF-I receptor.

Herein is further reported as an aspect a method for the production of a polypeptide comprising
- a) providing a cell comprising a nucleic acid encoding the polypeptide,
- b) providing a device as reported herein,
- c) cultivating the cell in the device in a cultivation medium wherein the agitator provides a turbulent flow within the cultivation vessel, and
- d) recovering the polypeptide from the cells or the cultivation medium and thereby producing a polypeptide.

In one embodiment the method is for the cultivating of a cell expressing a polypeptide encoded by a heterologous nucleic acid. In one embodiment the cultivating is a dialysis. In a further embodiment the cultivating is carried out in a submersed gassed stirred tank reactor. In another embodiment the cell is a eukaryotic cell. In also an embodiment the cell is a mammalian cell. In yet a further embodiment the cell is selected from a CHO cell, a BHK cell, an ISO cell, a COS cell, a PER.C6 cell, a Sp2/0 cell, and a HEK 293 cell. In one embodiment the polypeptide is an antibody. In another embodiment the antibody is an antibody against CD20, CD22, HLA-DR, CD33, CD52, EGFR, G250, GD3, HER2, PSMA, CD56, VEGF, VEGF2, CEA, Lewis Y antigen, the IL-6 receptor or the IGF-1 receptor.

DETAILED DESCRIPTION OF THE INVENTION

Herein reported is an agitator, which is a combination stirrer, comprising a radially-conveying element with one or more defined and integrated axially-conveying elements. The term "element" denotes a (functional) unit of stirrer blades which are in a fixed spatial configuration relative to one another with regard to distance and angle. A radially-conveying element denotes a stirrer which stirrer blades have no pitch with respect to the shaft axis. An axially-conveying element denotes a stirrer which stirrer blades have a pitch with respect to the shaft axis. The stirrer blades of the conveying elements are in one embodiment rectangular plates although other geometric forms can be used. The conveying direction of an element is denoted with respect to the shaft axis of the agitator. The axially-conveying elements, especially the individual blades thereof, are arranged as connecting pieces between the blades of the radially-conveying element. Also reported herein is a device comprising the agitator and a cultivation vessel. Further reported is the use of the agitator and the device in the cultivating of cells, in particular in a semi-continuous process such as e.g. internal or external dialysis. Exemplary embodiments of the agitators as reported herein are shown in FIG. 1.

Each of the conveying elements consists of a defined number of stirrer blades. Each blade is either directly connected to the rotary shaft or is connected to the rotary shaft via a hub. Each stirrer blade independent of the conveying element has an outer edge and an inner edge. The part of each stirrer blade that has the maximum distance to the shaft axis is denoted as tip of the blade. Each conveying element has an outer diameter and an inner diameter. For example, the outer diameter of an axially-conveying element is the maximum distance between the tips of opposing stirrer blades and the inner diameter of a radially-conveying element is the minimum distance between inner edges of opposing stirrer blades. In the agitator as reported herein the axially-conveying element(s) is(are) located within the radially-conveying element. Therefore, the outer diameter of the (all) axially-conveying element(s) is (are) equal to or less than the inner diameter of the radially-conveying element allowing the axially-conveying element(s) to be placed inside of the radially-conveying element. Some stirrer blades of (each of) the axially-conveying element(s) connect opposing stirrer blades of the radially-conveying element. As the radially-conveying elements are not directly connected to each other by this connection (each of) the axially-conveying element is individually, i.e. by itself, connected to the radially-conveying element. The connecting stirrer blades of the axially-conveying element do not need to be formed as stirrer blades for the entire distance between the stirrer blades of the radially-conveying element. Thus, the connecting blades of the axially-conveying element do not need to have the function of an axially-conveying over the entire distance, i.e. the do not have to be formed as a stirrer blade over the entire distance. That is the stirrer blade of the axially-conveying element may be shorter than the spatial distance to the inner edge of the stirrer blade of the radially-conveying element. This spatial gab is filled by a connecter that has no special form but provides for the connection of the tip of the blade of the axially-conveying element to the inner edge of the blade of the radially-conveying element.

The height h of the radially-conveying element is more than 10 times the height $h_{SB}$ of the axially-conveying elements. Thus, each of the axially-conveying elements can be placed at different positions relative to the height of the radially-conveying element. In one embodiment an axially-conveying element is located, i.e. it is placed, within a maximum distance of 80% of the total height h of the radially-conveying element relative to the head K of the agitator. This denotes that the axially-conveying element has a maximum distance from the head of the agitator of 0.8 h.

The rotary shall (also termed drive shall) extends through the longitudinal axis of the cultivation vessel in which the agitator is used.

The modification with respect to a primarily radially-conveying impeller, e.g. to an anchor impeller, is the (axially) downwards-conveying inclined-blade stirrer which is integrated in the upper and/or middle and/or lower region of the radially-conveying element. The agitator as reported herein provides among other things for an improved mixing of liquid solutions, for example in order to introduce correcting agents such as e.g. an acid or a base, nutrient solutions, anti-foaming agents or also $CO_2$ or $O_2$ via the liquid surface. Furthermore, the agitator reduces foam formation and in a dialysis process reduces biofouling and increases mass transfer by a direct orthogonal flow against the dialysis module. It has been found that the additional axially-conveying element(s) surprisingly does (do) not increase shear stress while at the same time improving the mixing and mass transport in the dialysis module.

In semi-continuous culturing processes, such as e.g. external or internal dialysis, substrates are fed to the reactor across a membrane and at the same time inhibiting components/metabolic products of the cultured cells are lead away. This exchange of material is by diffusion. The main influence factors therefore are the prevailing concentration difference, the membrane material, the membrane surface, the diffusion coefficients of the respective compounds inside the membrane material and the thickness of the phase interface which is determined by the flow against the membrane.

When dialysis is employed in high cell density fermentation it is a perfusion-like, semi-continuous process in which a (hollow fiber) dialysis module attached in the reactor provides the exchange area between the culture medium and fresh nutrient medium. The nutrient medium is pumped from a storage container through the dialysis module and thereafter returned again into the storage container (for a schematic diagram see FIG. 2). The dialysis module can be located outside the reactor (external dialysis) or within the reactor (internal dialysis). The same physical laws apply to both operating modes.

Thus, reported herein is a device comprising an agitator as reported herein and a cultivation vessel. In one embodiment the device also comprises a dialysis module. The components of the device are dimensioned in a way that they can exert their intended function, i.e. the cultivation vessel can take up the cultivation medium, the agitator can mix the medium and disperse added compound therein and the dialysis module can provide fresh medium and lead away metabolic compounds secreted by the cultivated cell. Thus, the agitator has a diameter that allows for an unhampered rotation within the vessel in the presence and absence of the dialysis module. It has been found that with the device as reported herein a high cell density cultivation as perfusion cultivation or as dialysis cultivation can be carried out advantageously. The cultivating is carried out in one embodiment at a rotation speed of the agitator at which a Reynolds-number independent constant power input to the cultivation medium can be achieved, i.e. during the cultivating a turbulent cultivation medium flow in the cultivation vessel is provided. It is possible with a device as reported herein to cultivate shear sensitive mammalian cells at a lower rotation speed of the agitator but at the same power input compared to known stirrers.

The form of the cultivation vessel is not limited. In one embodiment the cultivation vessel is a cylindrical vessel. In another embodiment the cultivation vessel is a stirred tank reactor. The cultivation vessel may have any dimension. In one embodiment the cultivation vessel has a working volume of from 5 l to 25,000 l.

Components from the fresh nutrient medium diffuse from the interior of the dialysis module through the semi-permeable hollow fiber membrane into the reactor and at the same time metabolites of the cultivated cells diffuse in the opposite direction from the reactor into the nutrient medium according to the concentration difference. The aim is to keep the absolute concentration of inhibiting metabolites in the reactor as low as possible (dilution) and at the same time to maintain the concentration of essential nutrients as long as possible at an optimal level for the culture. This results in improved culture conditions compared to a process without dialysis enabling to achieve higher maximum cell density or product titer.

The transport processes in the dialysis module can be described in an equivalent manner to mass transfer on a gas bubble by the two-film theory in conjunction with the first Fick's law. Thus, assuming linear gradients based on the exchange area $A_H$ of the hollow fiber dialysis module, the effective transferred diffusion flux $J_{eff}$ is according to equation 1:

$$J_{eff,i} = -D_{eff,i} \cdot A_H \cdot \frac{c_{2,i} - c_{1,i}}{x_2 - x_1} = -D_{eff,i} \cdot A_H \cdot \frac{\Delta c_i}{z_{eff}}. \quad \text{(Equation 1)}.$$

The driving force of diffusion is the concentration difference $\Delta c_i$ between the inside and outside of the dialysis module relative to the effective diffusion path $z_{eff}$. This effective diffusion path is composed of the individual paths through the inner laminar boundary layer on the inner side of the hollow fiber membrane of the dialysis module $\delta_{B1}$, through the hollow fiber membrane itself $\delta_M$ and through the outer laminar boundary layer on the outer side of the hollow fiber membrane in the reactor $\delta_{H1}$ (see FIG. 3). They generally depend on the size and shape of the diffusing molecule, the properties of the surrounding medium and the temperature. Separate mass transfer coefficients can be defined for the respective individual sections and from the summation of their reciprocals the total mass transfer resistance 1/k can be given according to equation 2:

$$\frac{1}{k} = \frac{1}{k_{HI}} + \frac{1}{k_M} + \frac{1}{k_{BI}}. \quad \text{(Equation 2)}.$$

The transport resistances in the laminar boundary layers on the inner and outer side of the hollow fiber membrane also depend on the flow against the follow fiber membrane. The better, i.e. the more perpendicular, the flow towards the membrane is the narrower the laminar boundary layers become and the lower are the corresponding transport resistances.

For a dialysis module in a reactor a direct dependency of the transport resistance of the outer laminar boundary layer on among others from the following factors exists:
the speed of rotation of the stirrer,
the type of stirrer,
the flow against the membranes,
the primary flow profile generated by the stirrer.

The resistance of the laminar boundary layer on the inner side of the hollow fiber membrane can be neglected due to the low inner diameter and the concomitant high flow velocities. Within this application the term "inner side of the hollow fiber membrane" denotes the side of the hollow fiber membrane which faces the storage container. The term "outer side of the hollow fiber membrane" denotes the side of the hollow fiber membrane which faces the reactor. The total mass transfer resistance is thus a series resistance to which mainly the resistance within the membrane and the resistance of the outer laminar boundary layer contribute (Rehm, et. al., Biotechnology—volume 3: Bioprocessing, VCH Weinheim, 1993). The total mass transfer coefficient k results from the reciprocal total mass transfer resistance and can be related to the surface area by multiplication with the volume-specific surface a of the hollow fiber dialysis module (ka value).

The following equation 3 can be used to describe the concentration time courses for the balance spaces reactor and storage container:

$$\frac{dc_R}{dt} = ka \cdot (c^* - c_R). \quad \text{(Equation 3)}.$$

The typical concentration time courses in the reactor $c_R$ and the storage container $c_V$ are shown in FIG. 4.

In general submerse gassed reactors are used in cell culture. In these cases a one-stage or two-stage axially-conveying stirrer system is mainly used. This generates a flow profile which is essentially parallel to the rotary shaft of the employed stirrer. Thus, in the arrangement as shown in FIG. 2 with the dialysis module parallel to the rotary shaft a direct flow against the dialysis module is not achieved.

This has a disadvantageous effect on the mass transport in the dialysis module (wider outer laminar boundary layer on the fiber surface).

A direct tangential or radial flow against the dialysis membrane has an advantageous effect which can for example be achieved by a standard anchor impeller. This impeller generates a flow which is directed directly onto the dialysis module or modules in the reactor and thus reduces the laminar boundary layer on the surface of the dialysis module(s). This simple radial flow is, however, disadvantageous for the other basic technical process functions in particular with regard to mixing the reactor and mass transfer especially in submersed gassed reactors. The gas can be introduced into the cultivation vessel e.g. via a pipe sparger or a ring sparger.

It has been found that the agitator (combination stirrer) as reported herein provides for a direct orthogonal flow against or towards the dialysis module and at the same time is suitable for mixing in liquids at/from the surface of the culture medium and for rapid total mixing of the culture medium whereby the shear stress for the cells in the reactor is almost not increased when compared to other stirring systems. It has turned out that the axial flow generated by the axially-conveying element(s), i.e. for example by inclined-blade stirrers, ensures a mixing of the culture medium in a short time. In addition shear sensitive cells such as mammalian cells can be cultivated at the same shear stress with increased mixing efficiency by using the agitator as reported herein.

The agitator as reported herein combines or integrates the properties of a radially-conveying element, i.e. for example of an anchor impeller, which are important for an application in dialysis processes with those of an axially-conveying element, such as e.g. an inclined-blade stirrer, which are important to fulfill the basic technical process requirements or functions. Exemplary embodiments of the agitator as reported herein are shown in FIGS. 1a) to 1f) in which one or more of the connecting elements of a radially-conveying element (anchor impeller) are designed as axially-conveying element fined-blade stirrer). Specific embodiments are shown in FIGS. 1a) to 1f).

The rotary speed of the stirrer n is used as a characteristic velocity and the stirrer width d is used as a characteristic length.

In fluid dynamics the Reynolds's number describes the ratio of inertial force to inner frictional force in a hydrodynamic system. Therefrom also statements can be made about the degree of turbulence of the moved medium. For stirred liquids the stirrer Reynolds's number is defined in equation 4 to be:

$$Re = \frac{n \cdot d^2}{v} = \frac{n \cdot d^2 \cdot \rho}{\eta}.$$ (Equation 4)

The Newton number (also referred to as power number) describes the ratio of resistance force to flow force and is thus a measure for the flow resistance of a stirrer in a stirred material and is described in equation 5:

$$Ne = \frac{P}{\rho \cdot n^3 \cdot d^5}.$$ (Equation 5)

Agitators with a low Newton number, such as propeller or inclined blade stirrers, convert the power input more efficiently in hydrodynamic output, i.e. fluid motion, than those with a high Newton number, such as rushton turbines.

A criterion for assessing the stirring processes in culture or cultivation processes is the mixing time. The "mixing time" in an inhomogeneous liquid-liquid mixture denotes the time which is required to achieve a defined homogeneity in the culture medium. Factors influencing the mixing time are the degree of mixing and the site of observation. The degree of mixing in turn depends on the reactor geometry, the stirrer geometry, the rotary frequency of the stirrer, and the substances of the stirred materials.

It is important for culture or cultivation processes that, as far as possible, all cells are optimally and uniformly supplied with the necessary substrates (such as nutrient medium, $O_2$) and that metabolites (such as overflow products, $CO_2$) are concomitantly led away. This means that repositories and sinks that may occur spatially as well as temporarily in the reactor have to be avoided or minimized in order to avoid damage to the cells. This can be achieved e.g. by using an adapted stirring system for mixing the reactor's contents. The mixing processes can be divided into the sub-processes micro-mixing and macro-mixing. Micro-mixing is defined as the molecular concentration adjustment due to diffusion or microturbulences; in contrast macro-mixing is defined as the convective coarse mixing caused by the stirrer (see e.g. Houcine, I., et al., Chem. Eng. Technol. 23 (2000) 605-613; Zlokarnik, M., "Rührtechnik Theorie und Praxis", Springer Publishers, Berlin Heidelberg, 1999). The degree of mixing can according to Henzler (Henzler, "Homogenisieren: Referenz-Rührsysteme und Methoden zur Erfassung der Homogenisierungseigenschaften von Rührsystemen", GVC Fachausschuß Mischvorgänge, 1998) be defined as follows in equation 6:

$$X_1 = 1 - \frac{\Delta a}{\overline{a}}.$$ (Equation 6).

In this equation $\overline{a}$ corresponds to the concentration of the tracer substance after a theoretically complete mixing and $\Delta a$ corresponds to the maximum difference between the local concentrations of the tracer substance at a time t. In general a degree of intermixing of $X_1=0.95$ is regarded as sufficient (see Henzler, supra). The mixing coefficient $C_H$ 0.95 as described in equation 7 is based on this degree of mixing and is the product of the mixing time $\theta_{0.95}$ and the rotary speed of the stirrer n that was used. Thus, it corresponds to the number of stirrer revolutions which are required after adding a correcting agent in order to achieve a degree of intermixing of 0.95 and results from equation 7:

$$C_{H\,0.95} = \Theta_{0.95} \cdot n$$ (Equation 7).

The mixing coefficients as shown in Table 1 and in extracts in FIG. 5 were determined by using the decolorizing method and result from the mixing time investigations (mixing characteristic see equation 7). A maximum relative error of ±15% was determined by multiple measurements.

TABLE 1

Mixing coefficients.

| Stirrer | H/D | d/D | $C_H$(Re) |
|---|---|---|---|
| agitator as reported herein (KR) | 1.6 | 0.4 | 31 |
| stirrer with a standard disk stirrer (1SSR) | 1.0 | 0.33 | 42 |
| stirrer with three separate inclined-blade stirrers (3SBR) | 1.6 | 0.33 | 64 |
| stirrer with three separate standard disk stirrers (3SSR) | 1.6 | 0.33 | 77 |

From the data presented in Table 1 it can be seen that the agitator as reported herein (KR) provides for a considerably shorter average mixing index of approximately 31 at a constant Reynolds's number for example in comparison to a stirrer combination consisting of three separate inclined-blade stirrers (3SBR) with an average mixing coefficient of 64. In the experiments it can be seen that the sodium thiosulfate is rapidly sucked into the liquid near the shaft of the agitator.

Another process-relevant parameter for the culture or cultivation of animal cells is the shear stress applied to the cell in the culture medium. Animal cell cultures are, among others, limited by the mechanical and hydrodynamic stress applied to the cells. The stress is, on the one hand, caused by the stirrer itself and, on the other hand, by the bubble aeration of the culture medium (see e.g. Wollny, S., and Sperling, R., Chem. Ing. Tec. 79 (2007) 199-208). For the turbulent flow regions which are mostly predominant in stirred tank reactors, the hydrodynamic stress is given by the Reynolds's stress approach according to equation 8 (Henzler, H. J. and Biedermann, A., Chem. Ing. Tec., 68 (1996) 1546-1561):

$$\tau_{turb} = \rho \cdot u'^2. \quad \text{(Equation 8)}.$$

According to equation 8 the main stress can be deduced as being due to the turbulent velocity fluctuation u' of the fluid elements.

The characterization of shear stress was carried out in non-gassed state with an incorporated dialysis module. The reference particle diameters $d_{VF}$ that were determined are shown in FIG. 6.

It can be seen that with the agitator as reported herein one of the biggest reference particle diameters can be obtained and thus this is the system with the lowest shear at a constant power input. Thus, at the same shear forces for example for the cultured cells it is possible to achieve a higher power input which, due to a higher number of revolutions, leads to higher turbulences and a higher flow against the dialysis module as well as to a better complete mixing.

In addition to NaCl, glucose was also used as a tracer substance to experimentally determine mass transfer coefficients. In general it could be shown that the mass transfer of the dialysis module is, on the one hand, influenced by the power input and, on the other hand, by the stirrer geometry, i.e. the primary generated flow mode. Tangential or radial flow profiles have proven to be particularly suitable with regard to reducing the outer laminar boundary layers around the hollow fiber dialysis membranes (higher mass transfer rates). The highest mass transfer coefficients can be achieved in each case by the agitator as reported herein.

FIG. 7 shows a comparison of the Newton numbers. As can be seen the agitator as reported herein provides for a considerably higher Newton number. At the same time it can be seen that the power number is independent of the Reynolds number.

Thus, the agitator provides for an increased power number independent of the Reynolds number when operated to produce a turbulent flow within the reaction vessel.

FIG. 8 shows that the highest mass transfer coefficients of the dialysis module at a constant volume-specific power input can be achieved with the agitator as reported herein. This is due to the radial flow generated by the stirrer according to the invention which, in comparison to the standard stirrer systems, allows a better flow against the hollow fiber dialysis module.

Compared to standard stirrer systems the agitator as reported herein provides for considerable advantages in the mixing (FIG. 5, Table 1), the generated shear stress (FIG. 6), as well as in the mass transfer coefficients in dialysis (FIG. 8). It is particularly remarkable that, despite the introduced modifications, no significantly higher shear stresses can be measured (see e.g. Pohlscheidt, M., et. al., Chem. Ing. Tec. 80 (2008) 821-830).

The abbreviations used in this application have the following meanings (see also FIG. 1a):
- b: width of the blades of the radially-conveying element
- d: agitator total outer diameter
- $d_w$: diameter of the shaft
- h: height of the stirrer blades of the radially-conveying element
- $h_m$: height of the fastening sleeve
- $h_{SB}$: height of an axially-conveying element
- $h_u$: height of the reducer
- Δh: height difference of two axially-conveying elements
- l: length of the stirrer blades of an axially-conveying element
- α: blade pitch of the blades of an axially-conveying element
- z: number of stirrer blades per stirrer
- $d_i$: inner distance between the stirrer blades of the radially-conveying element
- $h_{4/5}$: 4/5 height from above of h
- K: stirrer head, i.e. the highest point of the stirrer when it is not attached to a rotary shaft
- D: cultivation vessel inner diameter
- H: filling height of the cultivation vessel.

In one embodiment the ratio of the height difference (Δh) of two axially-conveying elements to the cultivation vessel diameter (D) is at least 0.75.

Herein is reported the use of the agitator as reported herein for the culture or cultivation of cells for the recombinant production of proteins or antibodies as an aspect. In one embodiment the culture is a dialysis. In a further embodiment the culture is carried out in a submersed gassed stirred tank reactor. In another embodiment the cell is a eukaryotic cell, in another embodiment a mammalian cell. In yet a further embodiment the cell is a CHO cell, a BHK cell, an NS0 cell, a COS cell, a PER.C6 cell, a Sp2/0 cell or a HEK 293 cell. In one embodiment the cell is selected from *Arthrobacter protophormiae, Aspergillus niger, Aspergillus oryzae, Bacillus amyloliquefaciens, Bacillus subtilis*, BHK cells, *Candida boidinii, Cellulomonas cellulans, Corynebacterium lilium, Corynebacterium glutamicum*, CHO cells, *E. coli, Geobacillus stearothermophilus, H. polymorpha*, HEK cells, HeLa cells, *Lactobacillus delbruekii, Leuconostoc mesenteroides, Micrococcus luteus*, MDCK cells, *Paenebacillus macerans, P. pastoris, Pseudomonas* species, *S. cerevisiae, Rhodobacter* species, *Rhodococcus erythropolis, Streptomyces* species, *Streptomyces anulatus, Streptomyces hygroscopicus*, Sf-9 cells, and *Xantomonas campestris*. In yet a further embodiment the antibody is an antibody against CD20, CD22, HLA-DR, CD33, CD52, EGFR, G250, GD3, HER2, PSMA, CD56, VEGF, VEGF2, CEA, Lewis Y antigen, IL-6 receptor or IGF-1 receptor.

The following example and figures are provided to illustrate the subject matter of the invention. The protective scope is defined by the attached patent claims. It is clear that modifications can be made on the subject matter of the disclosed methods without departing from the subject matter of the invention.

EXAMPLE 1

Cultivation Vessel

Figure 1:
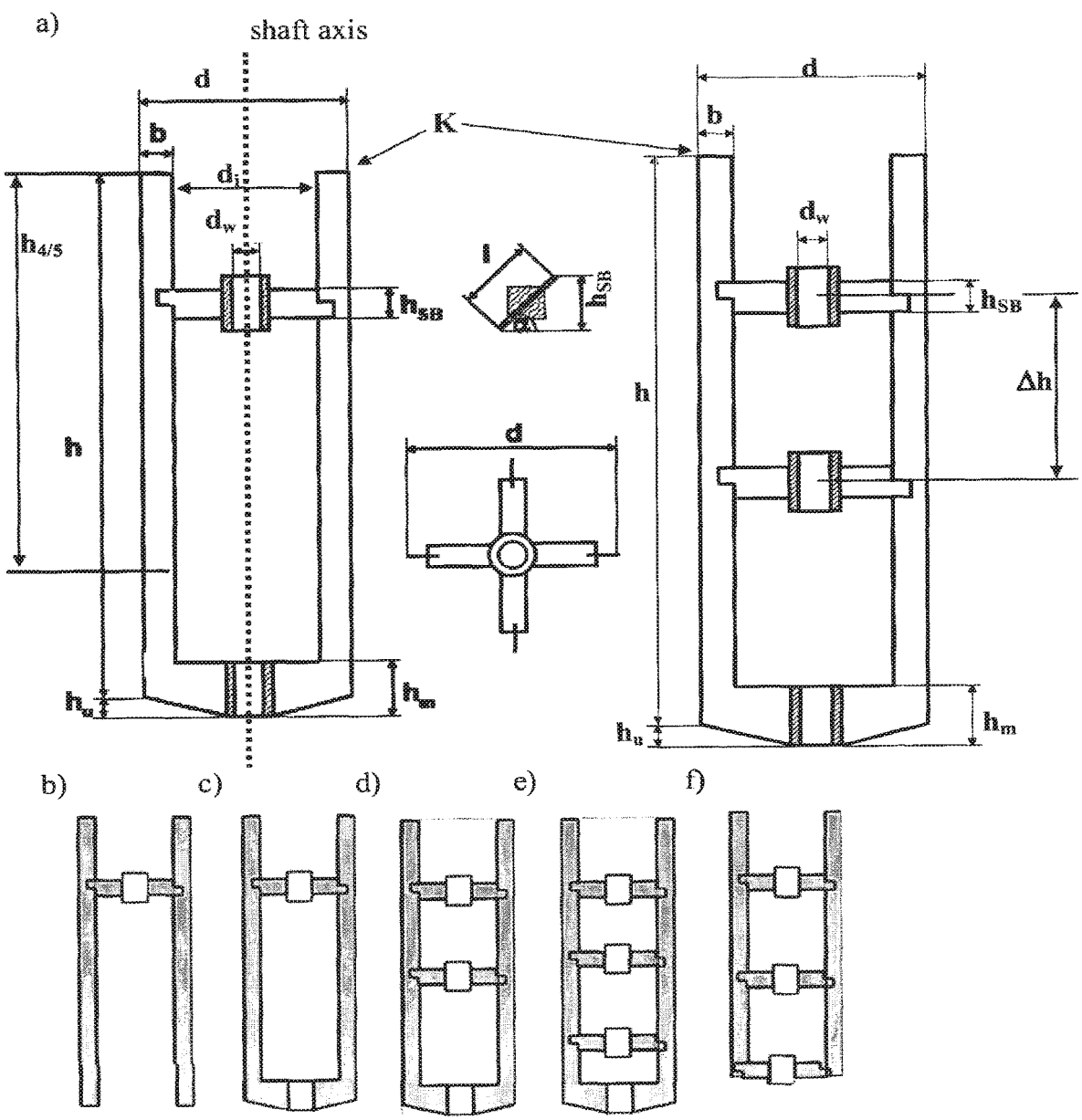
FIG. 1 Schematic diagram of various embodiments of the combination stirrer according to the invention; b: width of the stirrer blade; d: stirrer diameter; $d_w$: diameter of the rotary shaft; h: height of the stirrer blade of the radially-conveying stirrer; $h_n$: height of the fastening sleeve; $h_{SB}$: height of the axially-conveying stirrer; $h_u$: height of the reducer; l: length of the stirrer blade of the axially-conveying stirrer; α: blade pitch of the axially-conveying stirrer; z: number of stirrer blades per stirrer; $d_i$: inner distance between the stirrer blades of the radially-conveying stirrer; $h_{4/5}$: 4/5 height from above of h; K: stirrer head; a) general scheme of the agitator as reported herein; b) to f) embodiments of the agitator as reported herein; g) scheme of a radially conveying element seen from the top along the shaft axis; h) scheme of an axially conveying element seen from the top along the shaft axis; i) scheme of an embodiment of the agitator as reported herein seen from the top along the shaft axis showing the connection of opposing stirrer blades of the radially-conveying element via connecting stirrer blades of the axially-conveying element; j) scheme of an embodiment of the agitator as reported herein seen from the top along the shaft axis showing the connection of opposing stirrer blades of the radially-conveying element via connecting stirrer blades of the axially-conveying element wherein the diameter of the axially-conveying element is less than the inner diameter of the radially-conveying element and the spatial distance is bridged by a connector.
Figure 1:
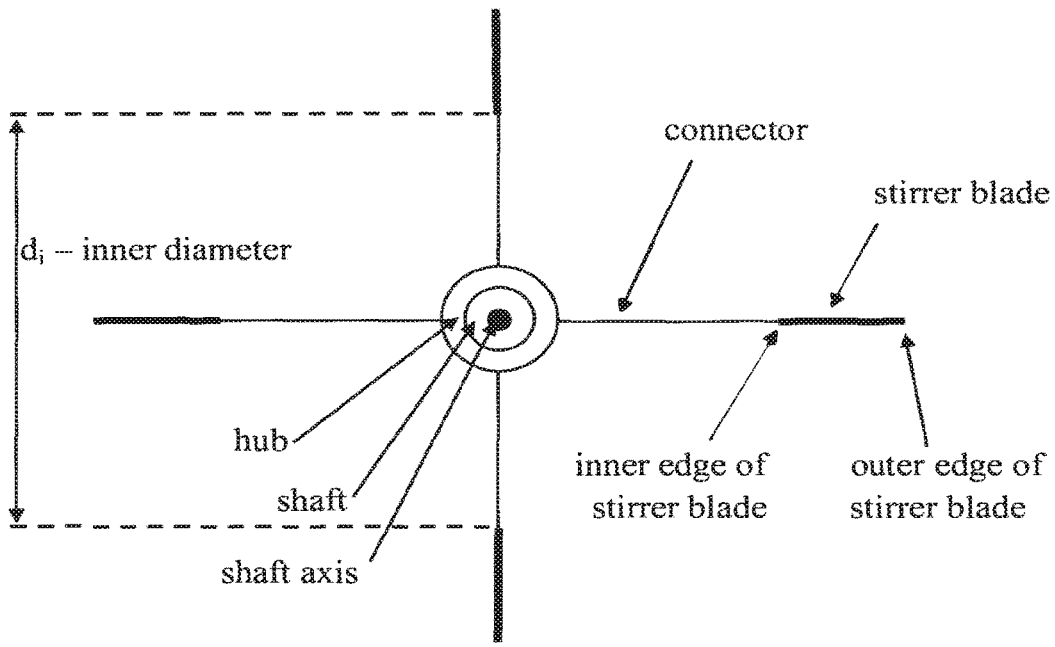
Figure 1:
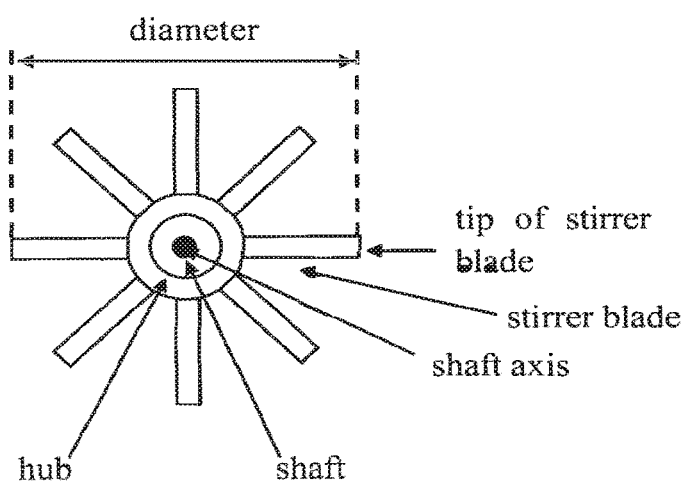
Figure 1:
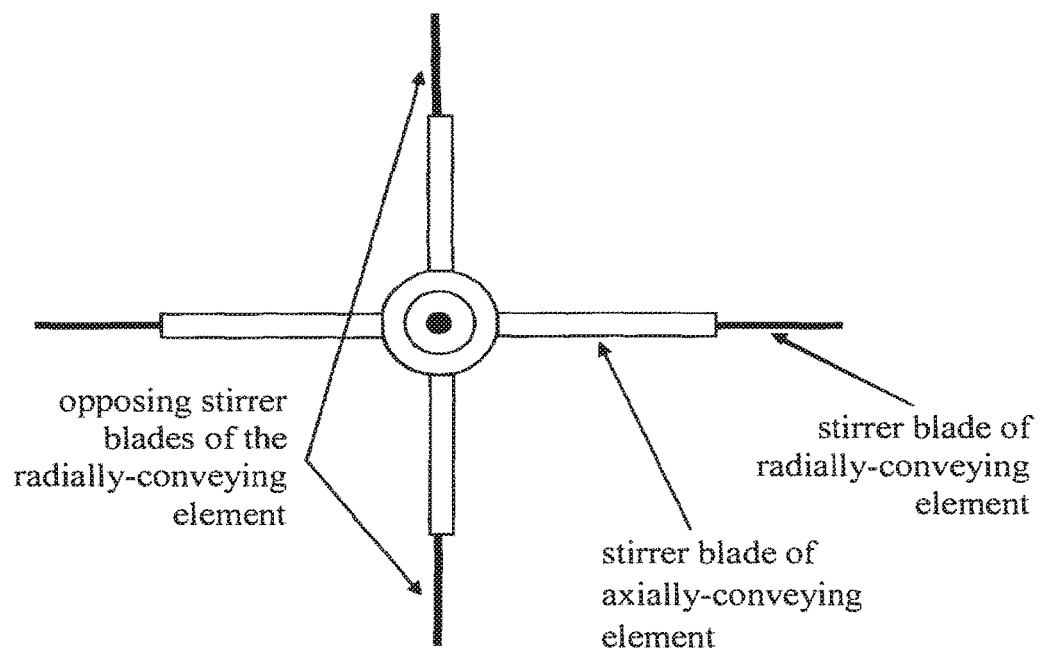
Figure 1:
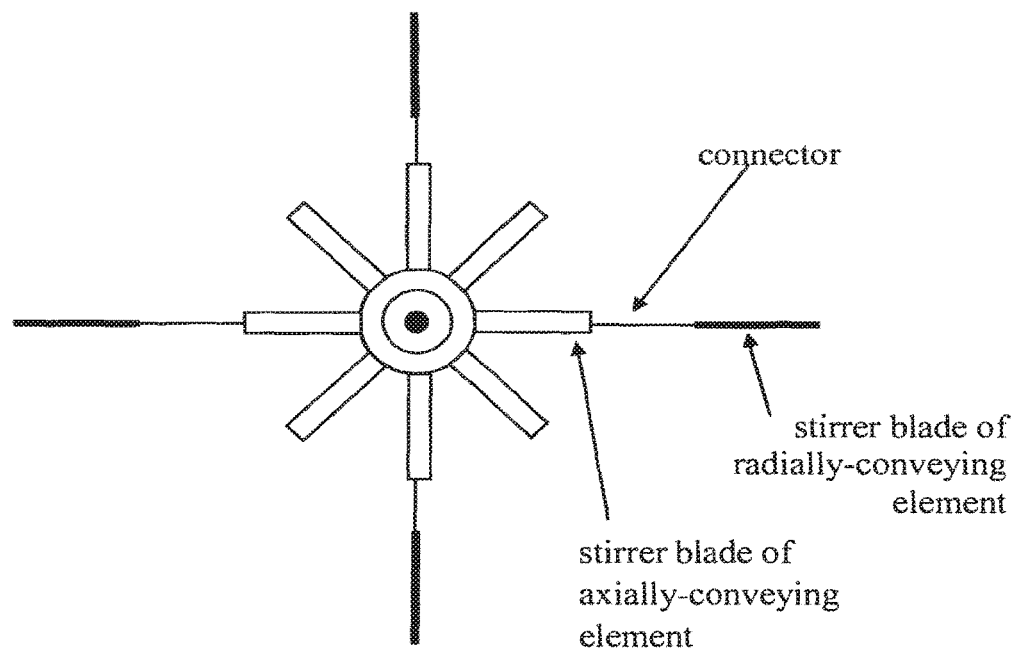
Figure 2:
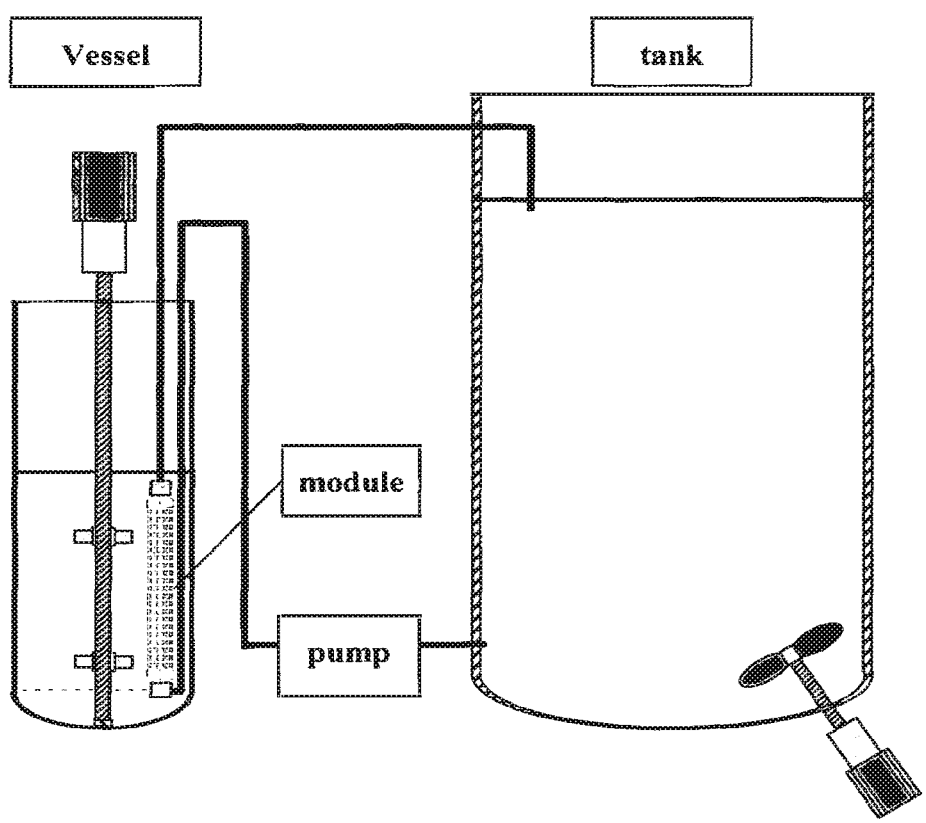
FIG. 2 Schematic diagram of a device for dialysis cultivation.
Figure 3:
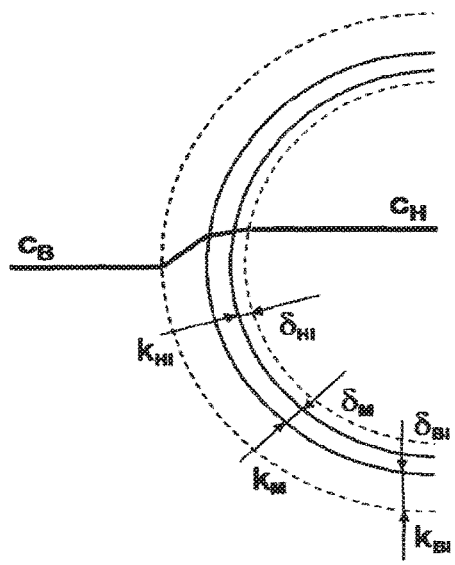
FIG. 3 Schematic diagram of the concentration gradients on the hollow fibers of the dialysis module.
Figure 4:
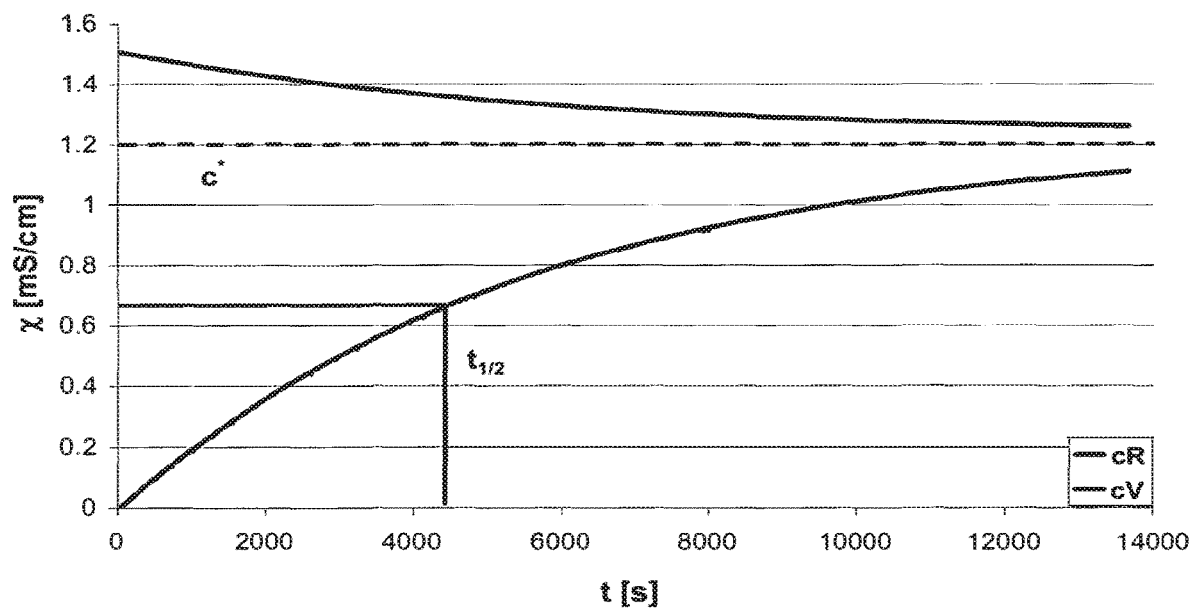
FIG. 4 Typical concentration time course in the reactor ($C_R$) and storage container ($C_V$).
Figure 5:
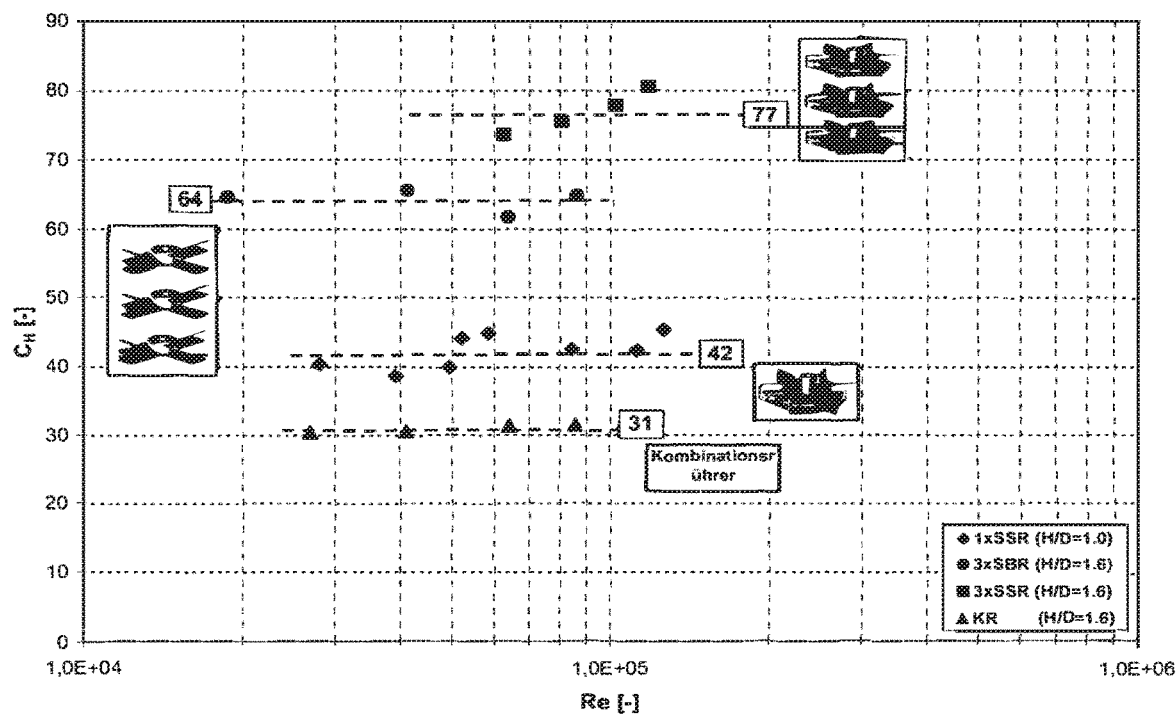
FIG. 5 Comparison of the mixing coefficients $C_H$ for different stirrer as a function of the Reynolds's number (Re); KR=combination stirrer as reported herein; SSR=standard disk stirrer; SBR=inclined-blade stirrer.
Figure 6:
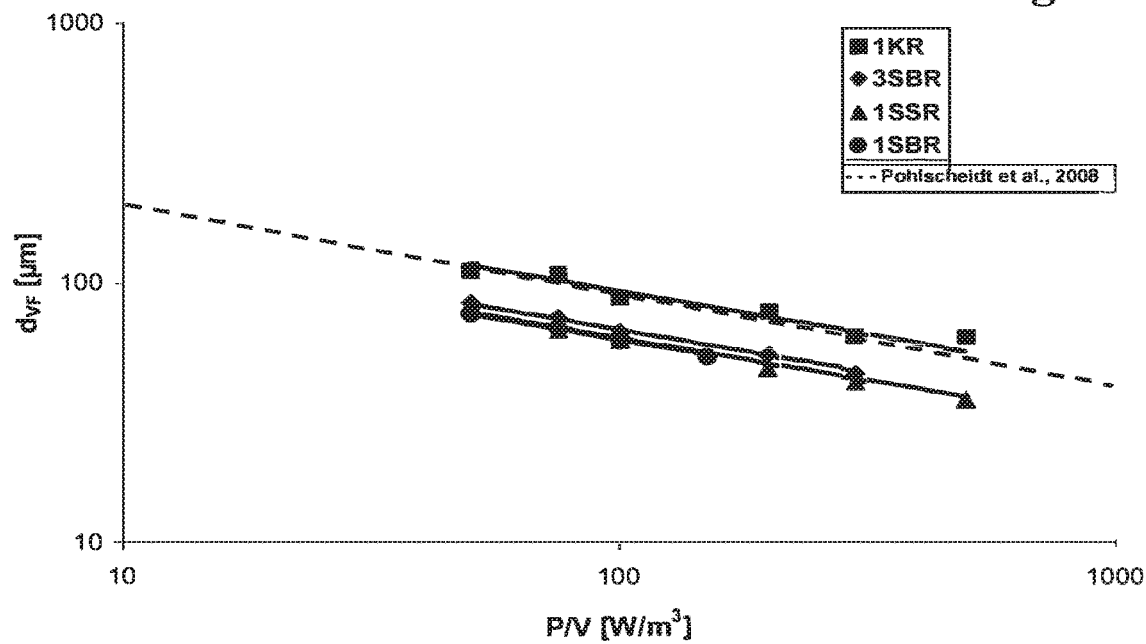
FIG. 6 Reference flake diameter $d_{VF}$ as a function of the volume-specific power input and stirrer configuration; KR=combination stirrer as reported herein; SSR=standard disk stirrer; SBR=inclined-blade stirrer; Pohlscheidt, M., et al.=Chem. Ing. Tec. 80 (2008) 821-830.
Figure 7:
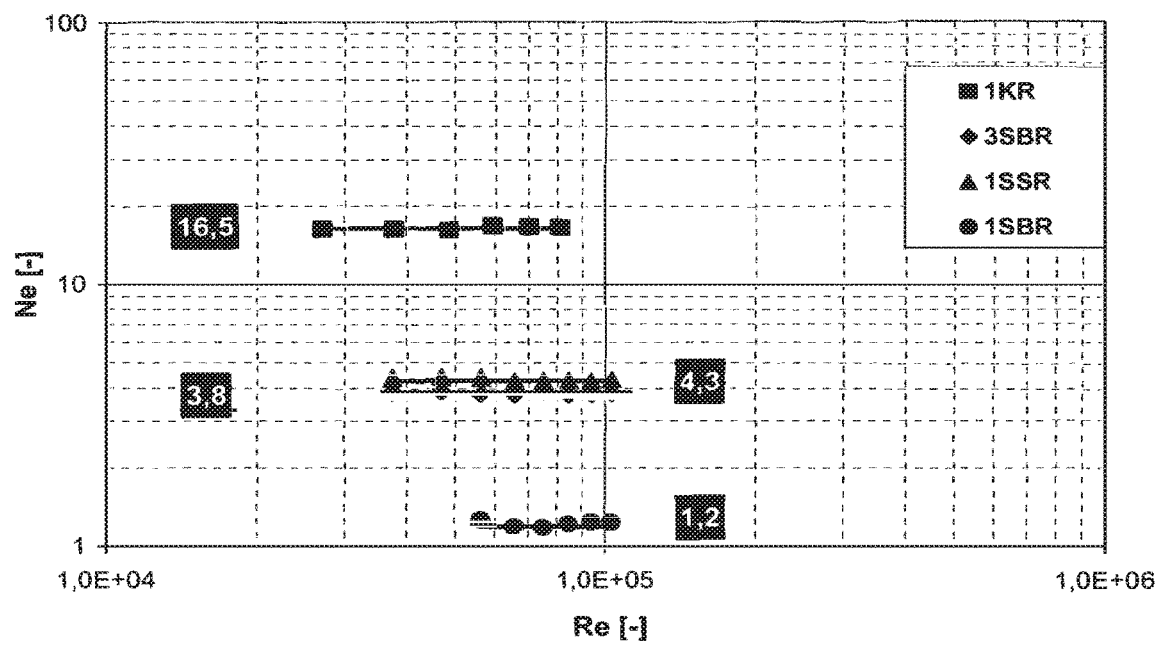
FIG. 7 Diagram of the power coefficient Ne of different stirrer as a function of the Reynolds's number (Re); KR=combination stirrer as reported herein; SSR=standard disk stirrer; SBR=inclined-blade stirrer.
Figure 8:
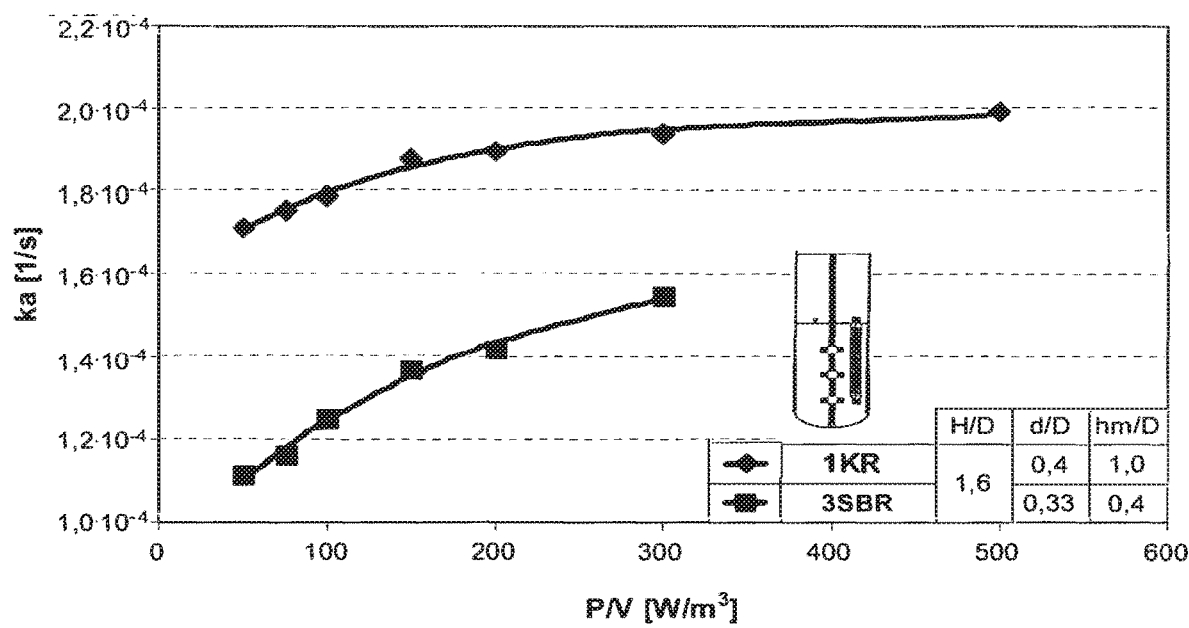
FIG. 8 Mass transfer coefficient $k_a$ in the dialysis as a function of the specific power input; KR=combination stirrer as reported herein; SBR=inclined-blade stirrer.

All investigations were carried out in a 100 l Plexiglas® model container (referred to as DN 440 in the following).

EXAMPLE 2

Power Input

The power input of different stirrer was determined by measuring the torque on the rotary shaft. A data processing system model GMV2 together with the torque sensor model DRFL-II-5-A (both from the "ETH Messtechnik" Company, Gschwend, Germany) were used to record the torque. For each stirrer system the torque was firstly recorded at various revolution speeds in the unfilled state ($M_{empty}$) and subsequently by means of a triplicate determination in the filled state ($M_{load}$) according to equation 9:

$$M = M_{load} - M_{empty}.\qquad\text{(Equation 9)}.$$

Afterwards the corresponding Newton number (Ne number) and the Reynolds's number (Re number) were calculated for each point. Since the Newton numbers for a stirrer system become constant in the turbulent flow region, the calculated Newton numbers were subsequently averaged in this region (Uhl, V. W. and Gray, J. B., Mixing Theory and Practice, Academic Press, 1966). This mean represents the total Newton number of the respective stirrer.

EXAMPLE 3

Homogenization

The homogenization was determined using the color change method as well as using the conductivity method.

The color change method is based on the decolorization of a starch solution stained with iodine-potassium iodide by addition of sodium thiosulfate (I, KI, starch, $Na_2S_2O_3$ obtained from the Carl Roth GmbH & Co KG Company, Karlsruhe, Germany). A one molar sodium thiosulfate solution and a one molar iodine-potassium iodide solution (Lugol's solution) as well as a starch solution at a concentration of 10 g/l were used as the starting solutions. In correspondence with the conductivity experiments, at least four speed steps were examined per stirrer (quadruplicate determinations per speed step) in which a maximum of four experiments were carried out per container filling amount. In each case the starch solution was added once per filling of the container. For each individual measurement the corresponding volume of the iodine-potassium iodide solution was firstly added and subsequently the sodium thiosulfate was added. The mixing time has been determined manually from the time point at which the sodium thiosulfate was added and one second was subtracted in each case in order to take the addition time into consideration. After completion of the measurement the container filling volume was titrated (neutralized) with iodine-potassium iodide in order to compensate for the excess of the previously added sodium thiosulfate.

In the conductivity method the mixing time is defined as the time from addition of an electrolyte solution to the time at which the measured conductivity fluctuations for the last time exceed a tolerance range of ±5% around the conductivity values which are reached in a stationary state. If several probes are used, the longest detected mixing time in each case is regarded as representative for the entire system.

A 30% (w/v) NaCl solution (NaCl crystalline, Merck KGaA Company, Darmstadt, Germany) was used as an electrolyte solution to determine the mixing time by the conductivity method. This was added in pulses onto the liquid surface at the rotary shaft of the stirrer and the volume per addition was selected such that the jumps in conductivity which resulted in a stationary state did not exceed 200 mS/cm.

For each stirrer at least four speed steps were examined. The mixing time was determined at least eight times per speed step and these eight values were averaged. The mixing coefficient of the respective stirrer systems is given as the mean of the mixing coefficients averaged per speed step. The conductivity was in each case measured by three 4-pole conductivity probes (TetraCon, WTW Company, Weilheim) at various radial or axial positions in the container. The conductivity signals were read out online via the measuring amplifier that was used (Cond813, Knick "Elektronische Messgeräte GmbH & Co, KG" Company, Berlin, Germany). The measured values were stored online and simultaneously for all probes by means of the software Paraly SW 109 (Knick "Elektronische Messgeräte GmbH & Co, KG" Company, Berlin, Germany) at a sampling rate of 5 seconds. After the series of measurements was completed the data were evaluated separately for each probe.

EXAMPLE 4

Shear Stress

A model particle system, the blue clay polymer flake system, was used to determine shear stress. This is a model particle system consisting of a cationic polymer (Praestol BC 650) and a clay mineral (blue clay) which is placed in the vessel. A flocculation reaction is started by adding Praestol BC 650 which generates flakes of a defined size. These flakes are subsequently broken up by the mechanical and hydrodynamic stress of the stirrer system. In the case of bubble-gassed systems they are additionally broken up by the energy dissipation when the bubbles are formed and burst. The average particle diameter of the model particle system was used as a measured variable to characterize the shear stress. In this case the change in the particle size was measured in situ by a Focused Beam Reflectance Measurement Probe from the Mettler Toledo Company (referred to as FBRM® in the following). The rates of change in particle size that were determined are a measure for the shear stress prevailing in the model system. The gradient of the rate of change of particle size becomes smaller during the course of the experiment but no equilibrium state is formed (particle comminution down to a diameter of the blue clay primary particles of ≈15 μm). For this reason an end flake diameter $d_{P50}'$ for the blue clay polymer flake system was determined according to the following criterion (equation 10):

$$\frac{d(d_{P50})}{dt} \leq 0.0055[\mu m/s] \rightarrow d_{P50} = d_{P50}'. \quad \text{(Equation 10)}$$

In order to ensure comparability of the end flake diameters at different power inputs and between different stirrers, the reference flake diameter was calculated as follows (equations 11 to 13):

$$d_{VF} = m \cdot d_{P50}' - b. \quad \text{(Equation 11)}$$

$$m = 1.3 \cdot 10^{-6} \cdot \left(\frac{P}{V}\right)^2 + 1.37 \cdot 10^{-3} \cdot \left(\frac{P}{V}\right) + 2.46. \quad \text{(Equation 12)}$$

$$b = 8.12 \cdot 10^{-5} \cdot \left(\frac{P}{V}\right)^2 + 6.48 \cdot 10^{-3} \cdot \left(\frac{P}{V}\right) + 76.9. \quad \text{(Equation 13)}$$

TABLE 2

Substances used to determine the particle stress (concentrations are based on the container fill volume).

| Ingredient | Concentration | Manufacturer |
| --- | --- | --- |
| Wittschlicker blue clay | 5 g/l | Braun Tonbergbau Co., Germany |
| Praestol 650 BC (solution 2 g/l) | 5 ml/l | Stockhaus GmbH & Co. KG, Krefeld, Germany |
| NaCl | 1 g/l | Merck KGaA, Darmstadt, Germany |
| CaCl$_2$ (solution 30 g/l) | — | Carl Roth GmbH & Co. KG, Karlsruhe, Germany |

Firstly the 100 l model container was filled with a corresponding volume (H/D ratio) of completely demineralized water (VE water) and maintained at a temperature of 20° C. Subsequently the conductivity was adjusted to a value of 1000 μS/cm by titration with a CaCl$_2$ solution. The conductivity was measured by a 4-pole conductivity probe (probe: TetraCon, WTW Co. Weilheim; measuring amplifier: Cond813, Knick "Elektronische Messgeräe GmbH & Co, KG" Company, Berlin, Germany). Afterwards the blue clay and the NaCl were added in appropriate amounts to the solution. Subsequently a homogenization phase took place at the highest speed with a duration of at least 20 minutes. The FBRM® probe (FBRM® Lasentec® D600L, Mettler-Toledo GmbH Co., Giessen, Germany) was mounted in the container perpendicular from above (immersion depth 300 mm) at a radial distance of 70 mm to the wall. The flocculation reaction was subsequently started by adding Praestol 650 BS at a defined speed. The measured values were recorded online by means of the program data acquisition control interface version 6.7.0 (Mettler-Toledo GmbH, Giessen, Germany). The reference flake diameter was determined from the measurement data. At least three power inputs were measured for each stirrer. In each case three measurements were carried out per power input.

EXAMPLE 5

Dialysis (Mass Transfer Liquid—Liquid)

A NaCl solution (NaCl crystalline, Merck KGaA Company, Darmstadt, Germany) was used as a tracer substance to determine the concentration half-life of the module (DIADYN-DP 070 F1 OL; MICRODYN-NADIR GmbH Company, Wiesbaden, Germany) in relation to the stirrer system that was used and the volume-specific power input. The tracer substance was adjusted in the storage container at the start of each experimental run to a base-line conductivity of 1500 μS/cm. The reactor was filled with completely demineralized water for each experimental run. The filling volume of the reactor was 100 l (H/D=1.6) and that of the storage container was 400 l (H/D=2.0) and both containers were maintained at a temperature of 20° C. at the start of each experiment. The conductivity in both containers was measured by a 4-pole conductivity probe (probe: TetraCon, WTW Co. Weilheim, Germany; measuring amplifier: Cond813, Knick "Elektronische Messgeräte GmbH & Co, KG" Company, Berlin, Germany). The sampling rate of the measurement amplifiers that were used was 5 seconds and the measurement values were stored online and simultaneously for all probes by means of the software Paraly SW 109 (Knick "Elektronische Messgeräte GmbH & Co, KG" Company, Berlin, Germany). The NaCl solution was circulated by means of a peristaltic pump between supply container and dialysis module (housing pump 520 U, Watson-Marlow GmbH, Company, Rommerskirchen, Germany) at a constant flow rate of 2.1 For the evaluation, probe 1 was used as a reference probe for the reactor and probe 3 was used as a reference probe for the storage container. The data of these two probes were evaluated by an evaluation routine. In each case at least six different power inputs in the reactor were investigated per stirrer.

In order to compare the mass transfer characteristics determined by means of the NaCl solution, additional measurements were carried out with a glucose solution as tracer substance. The experimental setup was not changed for this. A defined glucose concentration (glucose solid, Merck KGaA. Company, Darmstadt, Germany) at a concentration of 3 g/l was provided in the storage container. The glucose concentration was determined manually and simultaneously for the storage container and reactor at a time interval of 10 minutes by means of a blood sugar measuring instrument (ACCU-CHEK® Aviva, Roche Diagnostics GmbH Company, Mannheim, Germany).

The invention claimed is:

1. An agitator configured to improve mixing and mass transport within a cell cultivation vessel, comprising:
    a shaft comprising a shaft axis;
    one anchor impeller comprising at least two opposing stirrer blades, wherein the stirrer blades of the anchor impeller have no pitch with respect to the shaft axis; and
    one or more inclined-blade stirrers each comprising at least two stirrer blades, wherein the stirrer blades of each of the inclined-blade stirrers have a pitch with respect to the shaft axis,
    wherein the stirrer blades of the anchor impeller are parallel to each other and to the shaft axis,
    wherein an outer diameter of each inclined-blade stirrer is equal to or less than an inner diameter of the anchor impeller, the outer diameter of each inclined-blade stirrer is a maximum distance between tips of opposing stirrer blades of each inclined-blade stirrer and the inner diameter of the anchor impeller is a minimum distance between inner edges of opposing stirrer blades of the anchor impeller,
    wherein all inclined-blade stirrers are individually connected to the anchor impeller,
    wherein all inclined-blade stirrers are located within the anchor impeller, and
    wherein the anchor impeller and the inclined-blade stirrers all have a fixed spatial orientation relative to each other with regard to distance and angle.

2. The agitator according to claim 1, wherein the number of inclined-blade stirrers is 1 or 2 or 3.

3. The agitator according to claim 1, wherein one of the inclined-blade stirrers is located at a maximum distance of 80% from a top of the blades of the anchor impeller and/or one of the inclined-blade stirrers is located at a maximum distance of 20% from a top of the blades of the anchor impeller.

4. The agitator according to claim 1, wherein the opposing stirrer blades of the anchor impeller are linked to each other by two opposite stirrer blades of one or more of the inclined-blade stirrers.

5. The agitator according to claim 1, wherein the pitch of the stirrer blades of the inclined-blade stirrers is between 10° and 80° relative to the shaft axis of the agitator.

6. The agitator according to claim 1, wherein the anchor impeller has up to 8 stirrer blades.

7. The agitator according to claim 1, wherein the inclined-blade stirrers have independent of each other up to 10 stirrer blades.

8. The agitator according to claim 1, wherein the anchor impeller has a height of at least 200 mm.

* * * * *